(12) United States Patent
Chen et al.

(10) Patent No.: US 8,293,262 B2
(45) Date of Patent: *Oct. 23, 2012

(54) MEDICAL DEVICES HAVING MULTIPLE LAYERS

(75) Inventors: John Jianhua Chen, Plymouth, MN (US); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 213 days.

This patent is subject to a terminal disclaimer.

(21) Appl. No.: 12/835,157

(22) Filed: Jul. 13, 2010

(65) Prior Publication Data

US 2010/0280452 A1 Nov. 4, 2010

Related U.S. Application Data

(63) Continuation of application No. 10/849,742, filed on May 20, 2004, now Pat. No. 7,758,892.

(51) Int. Cl.
*A61F 2/92* (2006.01)
(52) U.S. Cl. ........................................ 424/423
(58) Field of Classification Search .................. None
See application file for complete search history.

(56) References Cited

U.S. PATENT DOCUMENTS

| | | | |
|---|---|---|---|
| 5,208,111 A | 5/1993 | Decher et al. | |
| 5,358,486 A | 10/1994 | Saab | |
| 5,755,690 A | 5/1998 | Saab | |
| 5,836,926 A | 11/1998 | Peterson et al. | |
| 6,004,289 A | 12/1999 | Saab | |
| 6,024,722 A | 2/2000 | Rau et al. | |
| 6,124,007 A | 9/2000 | Wang et al. | |
| 6,328,925 B1 | 12/2001 | Wang et al. | |
| 6,406,457 B1 | 6/2002 | Wang et al. | |
| 6,492,096 B1 | 12/2002 | Liu et al. | |
| 6,790,425 B1 | 9/2004 | Smalley et al. | |
| 2001/0046564 A1 | 11/2001 | Kotov | |
| 2002/0037383 A1 | 3/2002 | Spillman | |
| 2002/0061326 A1 | 5/2002 | Li et al. | |
| 2003/0065355 A1 | 4/2003 | Weber | |
| 2003/0093107 A1 | 5/2003 | Parsonage et al. | |
| 2003/0099798 A1 | 5/2003 | George et al. | |
| 2003/0143350 A1 | 7/2003 | Jimenez | |
| 2003/0157260 A1 | 8/2003 | Rubner et al. | |

(Continued)

FOREIGN PATENT DOCUMENTS

EP 0972563 1/2000

(Continued)

OTHER PUBLICATIONS

Chung, A.J. and Rubner, M.F., "Methods of Loading and Releasing Low Molecular Weight Cationic Molecules in Weak Polyelectrolyte Multilayer Films," Langmuir 2002, 18, 1176-1183.

(Continued)

*Primary Examiner* — Carlos Azpuru
(74) *Attorney, Agent, or Firm* — Vidas, Arrett & Steinkraus, P.A.

(57) ABSTRACT

Described herein are medical devices which are configured for implantation or insertion into a subject, preferably a mammalian subject. The medical devices contain one or more multilayer regions, which contain: (a) one or more (typically a plurality of) charged nanoparticle layers and (b) one or more (typically a plurality of) charged polyelectroyte layers. Such multilayers have a number of desirable attributes, including high strength, non-compliance, and flexibility. Also described herein are methods of making such devices.

20 Claims, 3 Drawing Sheets

U.S. PATENT DOCUMENTS

| | | |
|---|---|---|
| 2003/0175517 A1 | 9/2003 | Voigt et al. |
| 2003/0219909 A1 | 11/2003 | Lally et al. |
| 2003/0229184 A1 | 12/2003 | Acquarulo, Jr. et al. |
| 2004/0006359 A1 | 1/2004 | Laguna |
| 2004/0023317 A1 | 2/2004 | Motamedi et al. |
| 2004/0098021 A1 | 5/2004 | Laguna |
| 2005/0015046 A1 | 1/2005 | Weber et al. |

FOREIGN PATENT DOCUMENTS

| | | |
|---|---|---|
| WO | 9913924 | 3/1999 |
| WO | 9947252 | 9/1999 |
| WO | 0044507 | 8/2000 |
| WO | 0178906 | 10/2001 |
| WO | 02056930 | 7/2002 |
| WO | 03035278 | 5/2003 |
| WO | 03103854 | 6/2003 |
| WO | 2004047880 | 6/2004 |
| WO | 2004069169 | 8/2004 |

OTHER PUBLICATIONS

Frank Caruso et al., "Microencapsulation of Uncharged Low Molecular Weight Organic Materials by Polyelectrolyte Multilayer Self-Assembly," Langmuir 2000, 16, 8932-8936.

Gi-Ra, Yi et al., Ordered Macroporous Particles by Colloidal Templating, Chem. Mater 2001, 13, 2613-2618.

Shchukin, D.G. et al., Micron-Scale Hollow Polyelectrolyte Capsules with Nanosized Magnetic Fe3O4 Inside, Materials Letters 57, 1743-1747, 2003.

Radtchenko, I.L. et al., A Novel Method for Encapsulation of Poorly Water-soluble Drugs: Precipitation in Polyelectrolyte Multilayer Shells, International Journal of Pharmaceutics, 242, 219-223 (2002).

Radtchenko, I.L. et al., "Assembly of Alternated Multivalent Ion/Polyelectrolyte Layers on Colloidal Particles. Stability of the Multilayers and Encapsulation of Macromolecules into Polyelectrolyte Capsules," Journal of Colloid and Interface Science, 230, 272-280 (2000).

Winky L. W. Hau, "Surface-Chemistry Technology for Microfluidics," J. Micromech Microeng. 13 (2003) 272-278.

Radtchenko et al., "Incorporation of Macromolecules into Polyelectrolyte Micro and Nanocapsules via Surface Controlled Precipitation on Colloidal Particles," Colloids and Surfaces A. Physicochemical and Engineering Aspects 202 (2002) 127-133.

Moya, S. et al., "Polyelectrolyte multilayer capsules templated on biological cells: core oxidation influences layer chemistry," Colloids and Surfaces A Physicochemical and Engineering Aspects 183-185 (2001) 27-40.

Antipov, Alexei A. et al., "Polyelectorlyte multilayer capsule permeability control," Colloids and Surfaces A Physicochemical and Engineering Aspects 198-200 (2002) 535-541.

Qiu, Xingping et al., Studies on the Drug Release Properties of Polysaccharide Multilayers Encapsulated Ibuprofen Microparticles, Langmuir 2001, 17, 5375-5380.

Antipov, Alexei A. et al., Sustained release Properties of Polyelectrolyte Multilayer Capsules, J. Phys. Chem. B2001, 105, 2281-2284, Oct. 27, 2000.

https://engineering.purdue.edu.BME/Seminars12003/july_14_ html, Graduate Seminar, "Stent coating for drug delivery: Coating polymeric micelles using polyelectrolytes," Purdue University Biomedical Engineering Seminar, 2003, 1-2, Jul. 14, 2003.

Pommersheim, Rainer; Schrezenmeir, Jurgen; Vogt, Walter, "Immobilization of enzymes by multilayer microcapsules," Macromol. Chem. Phys. vol. 195, 1994, pp. 1557-1567.

Billing, P.; Pommersheim, Walter; Vogt, W., "Encapsulation of cytochrome C by multilayer microcapsules. A model for improved enzyme immobilization," Journal of Membrane Science, vol. 129, 1997, pp. 283-287.

Sukhorukov, Gleb B.; Shchukin, Dmitry G.; Dong, Wen-Fei; Mohwald, Helmut; Lulevich, Valentin VI; Vinogradova, Olga I., "Comparative Analysis of Hollow and Filled Polyelectroyte Microcapsules Templated on Melamine Formaldehyde and Carbonate Cores," Macromol. Chem. Phys. 2004, vol. 205. pp. 530-535.

Sastry, Murali; Kumar, Ashavani; Datar, Suvarna; Dharmadhikari, C.V.; Ganesh, Krishna N., "DNA-mediated electrostatic assembly of gold nanoparticles into linear arrays by a simple drop-coating procedure," Applied Physics Letters, vol. 78, No. 19, May 7, 2001, pp. 2943-2945.

Mamedov, Arif A.; Kotov, Nicholas A.; Prato, Maurizio; Guldi, Dirk M.; Wicksted, James P.; Hirsch, Andreas, "Molecular design of strong single-wall carbon nanotubelpolyelectrolyte multilayer composites," Nature Publishing Group, Nov. 2002, vol. 1, pp. 190-194.

MEDICAL DEVICES HAVING MULTIPLE LAYERS

CROSS-REFERENCE TO RELATED U.S. APPLICATIONS

This application is a Continuation of and claims priority to U.S. patent application Ser. No. 10/849,742, filed May 20, 2004, the entire contents of which are hereby incorporated herein by reference.

FIELD OF THE INVENTION

The present invention relates to the layer-by-layer assembly of multilayer regions for implantable and insertable medical devices, and more particularly, to the formation of multilayer regions that contain a plurality of nanoparticle layers for such devices.

BACKGROUND OF THE INVENTION

Various medical devices are known which are configured for implantation or insertion into a subject. As such theses devices have attendant mechanical requirements.

For example, balloons mounted on the distal ends of catheters are widely used in medical treatment. A balloon may be used, for example, to widen a vessel into which the catheter is inserted or to force open a blocked vessel. The requirements for the strength and size of the balloon vary widely depending on the balloon's intended use and the vessel size into which the catheter is inserted. Perhaps the most demanding applications for such balloons are in balloon angioplasty (e.g., percutaneous transluminal coronary angioplasty or "PCTA") in which catheters are inserted for long distances into extremely small vessels and are used to open stenoses of blood vessels by balloon inflation. These applications require extremely thin-walled, high-strength balloons having predictable inflation properties. Thin walls are necessary, because the balloon's wall thickness limits the minimum diameter of the distal end of the catheter and therefore determines the ease of passage of the catheter through the vascular system and the limits on treatable vessel size. High strength is necessary because the balloon is used to push open stenoses, and the thin wall of the balloon must not burst under the high internal pressures necessary to accomplish this task (e.g., 10 to 25 atmospheres). The balloon elasticity should be relatively low (i.e., the balloon should be substantially non-compliant), so that the diameter is easily controllable (i.e., small variations in pressure should not cause wide variations in diameter, once the balloon is inflated).

As another example, intraluminal stents or stent grafts are commonly inserted or implanted into body lumens. In one common mode of implantation, the stent is provided in a compact state over an inflatable balloon. This assembly is then advanced to the desired site within a body lumen, whereupon the balloon is inflated and the stent or stent graft is expanded to support the vessel walls. In this process, the stent or stent graft is subjected to substantial forces and therefore must be mechanically robust.

SUMMARY OF THE INVENTION

The above and other challenges are addressed by the present invention.

According to one aspect of the present invention, medical devices are provided which are configured for implantation or insertion into a subject. The medical devices contain one or more multilayer regions, which contain the following: (a) one or more charged nanoparticle layers and (b) one or more charged polyelectroyte layers.

According to another aspect of the present invention, methods are provided for making such medical devices. These methods comprise applying a series of charged layers over a substrate. Each successive layer in the series is opposite in charge relative to the previously applied layer. Furthermore, the series of charged layers that are applied over the substrate include the following: (a) one or more charged nanoparticle layers and (b) one or more charged polyelectroyte layers.

An advantage of the present invention is that multilayer medical devices and medical device components can be provided, which are very thin and flexible, have very high strength, and are substantially non-compliant.

These and other aspects, embodiments and advantages of the present invention will become immediately apparent to those of ordinary skill in the art upon reading the disclosure to follow.

DETAILED DESCRIPTION OF THE INVENTION

According to one aspect of the present invention, medical devices are provided, which are adapted for implantation or insertion into a subject and which include one or more multilayer regions. The multilayer regions contain a plurality of alternating, oppositely charged layers, including the following: (a) one or more (typically a plurality of) charged nanoparticle layers, each containing charged nanoparticles, and (b) one or more (typically a plurality of) charged polyelectroyte layers, each containing one or more charged polyelectrolyte species. The nanoparticle layers and the polyelectrolyte layers have charges that are opposite to the charges of adjacent layers.

Examples of medical devices for the practice of the present invention include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, vascular valves, biopsy devices, patches for delivery of therapeutic agent to intact skin and broken skin (including wounds); tissue engineering scaffolds for cartilage, bone, skin and other in vivo tissue regeneration, as well as any coated substrate (which can comprise, for example, glass, metal, polymer, ceramic and combinations thereof) that is implanted or inserted into the body.

The medical devices of the present invention include medical devices that are used for diagnostics, systemic treatment, or for the localized treatment of any mammalian tissue or organ. Examples include tumors; organs including the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; dermal tissue; cartilage; and bone.

As used herein, "treatment" refers to the prevention of a disease or condition, the reduction or elimination of symptoms associated with a disease or condition, or the substantial or complete elimination a disease or condition. Typical subjects are mammalian subjects, more typically human subjects.

The multilayer regions of the present invention can be assembled using layer-by-layer techniques. Layer-by-layer techniques can be used to coat a wide variety of substrates using charged materials via electrostatic self-assembly. In the layer-by-layer technique, a first layer having a first surface charge is typically deposited on an underlying substrate, followed by a second layer having a second surface charge that is opposite in sign to the surface charge of the first layer, and so forth. The charge on the outer layer is reversed upon deposition of each sequential layer.

Substrates for the practice of the present invention include substrates that are incorporated into the finished medical device, as well as substrates that merely acts as templates for the layer-by-layer technique, but which are not found in the finished device (although a residue of the substrate will remain in certain embodiments). The substrates are commonly formed from ceramic, metallic, polymeric and other high molecular weight materials, including stable and disintegrable materials.

Ceramic substrates may be selected, for example, from substrates containing one or more of the following: metal oxides, including aluminum oxides and transition metal oxides (e.g., oxides of titanium, zirconium, hafnium, tantalum, molybdenum, tungsten, rhenium, and iridium); silicon-based ceramics, such as those containing silicon nitrides, silicon carbides and silicon oxides (sometimes referred to as glass ceramics); calcium phosphate ceramics (e.g., hydroxyapatite); and carbon-based, ceramic-like materials such as carbon nitrides.

Metallic substrates may be selected, for example, from substrates containing one or more of the following: metal alloys such as cobalt-chromium alloys, nickel-titanium alloys (e.g., nitinol), cobalt-chromium-iron alloys (e.g., elgiloy alloys), nickel-chromium alloys (e.g., inconel alloys), and iron-chromium alloys (e.g., stainless steels, which contain at least 50% iron and at least 11.5% chromium), and noble metals such as silver, gold, platinum, palladium, iridium, osmium, rhodium, titanium, tungsten, and ruthenium.

Substrates containing polymers and other high molecular weight materials may be selected, for example, from substrates containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly lactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylenetetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid, various waxes, including low melting point waxes used for dental engineering (e.g., for so-called "lost wax" techniques); as well as blends and further copolymers of the above.

Certain substrates are inherently charged and thus readily lend themselves to layer-by-layer assembly.

To the extent that the substrate does not have an inherent net surface charge, a surface charge may nonetheless be provided. For example, where the substrate to be coated is conductive, a surface charge can be provided by applying an electrical potential to the same. Once a first polyelectrolyte layer is established in this fashion, a second polyelectrolyte layer having a second surface charge that is opposite in sign to the surface charge of the first polyelectrolyte layer can readily be applied, and so forth.

As another example, the substrate can be provided with a positive charge by covalently attaching functional groups having positive charge (e.g., amine, imine or another basic groups) or functional groups having a negative charge (e.g., carboxylic, phosphonic, phosphoric, sulfuric, sulfonic, or other acid groups) using methods well known in the art.

As another example, a surface charge can be provided on a substrate by exposing the substrate to a charged amphiphilic substance. Amphiphilic substances include any substance having hydrophilic and hydrophobic groups. Where used, the amphiphilic substance should have at least one electrically charged group to provide the substrate surface with a net electrical charge. Therefore, the amphiphilic substances that are used herein can also be referred to as an ionic amphiphilic substances.

Amphiphilic polyelectrolytes are used as ionic amphiphilic substances in some embodiments. For example, a polyelectrolyte comprising charged groups (which are hydrophilic) as well as hydrophobic groups, such as polyethylenimine (PEI) or poly(styrene sulfonate) (PSS), can be employed. Cationic and anionic surfactants are also used as amphiphilic substances in some embodiments. Cationic surfactants include quaternary ammonium salts ($R_4N^+X^-$), where R is an organic radical and where $X^-$ is a counter-anion, e.g. a halogenide, for example, didodecyldimethylammonium bromide (DDDAB), alkyltrimethylammonium bromides such as hexadecyltrimethylammonium bromide (HDTAB), dodecyltrimethylammonium bromide (DTMAB), myristyltrimethylammonium bromide (MTMAB), or palmityl trimethylammonium bromide, or N-alkylpyridinium salts, or tertiary amines ($R_3NH^+X^-$), for example, cholesteryl-3β-N-(dimethyl-aminoethyl)-carbamate or mixtures thereof. Anionic surfactants include alkyl or olefin sulfate ($R-OSO_3M$), for example, a dodecyl sulfate such as sodium dodecyl sulfate (SDS), a lauryl sulfate such as sodium lauryl sulfate (SLS), or an alkyl or olefin sulfonate ($R-SO_3M$), for example, sodium-n-dodecyl-benzene sulfonate, or fatty acids ($R-COOM$), for example, dodecanoic acid sodium salt, or phosphoric acids or cholic acids or fluoro-organics, for example, lithium-3-[2-(perfluoroalkyl)ethylthio]propionate or mixtures thereof, where R is an organic radical and M is a counter-cation.

Hence, in some embodiments, a surface charge is provided on a substrate by adsorbing cations (e.g., protamine sulfate, polyallylamine, polydiallyldimethylammonium species, polyethyleneimine, chitosan, gelatin, spermidine, albumin, among many others) or by adsorbing anions (e.g., polyacrylic acid, sodium alginate, polystyrene sulfonate, eudragit, gelatin [gelatin is an amphiphilic polymer, hence it fits in both categories depending how it is being prepared], hyaluronic acid, carrageenan, chondroitin sulfate, carboxymethylcellulose, among many others) to the surface of the substrate as a first charged layer. Although full coverage may not be obtained for the first layer, once several layers have been deposited, a full coverage should ultimately be obtained, and the influence of the substrate is expected to be negligible. The feasibility of this process has been demonstrated on glass substrates using charged polymeric (polyelectrolyte) materials. See, e.g., "Multilayer on solid planar substrates," *Multilayer thin films. sequential assembly of nanocomposite materials*, Wiley-VCH ISBN 3-527-30440-1, Chapter 14; and "Surface-chemistry technology for microfluidics," Hau, Winky L. W. et al. *J. Micromech. Microeng.* 13 (2003) 272-278.

The species for establishing a surface charge can be applied to the substrate by a variety of techniques. These techniques include, for example, spraying techniques, dipping techniques, roll and brush coating techniques, techniques involving coating via mechanical suspension such as air suspension, ink jet techniques, spin coating techniques, web coating techniques and combinations of these processes. The choice of the technique will depend on the requirements at hand. For example, dipping and spraying techniques (without masking) can be employed, for instance, where it is desired to apply the species to an entire substrate. On the other hand, roll coating, brush coating and ink jet printing can be employed, for instance, where it is desired to apply the species only certain portions of the substrate (e.g., in the form of a pattern).

Once a sufficient charge is provided on a substrate, it can be readily coated with a layer of an oppositely charged material. Multilayer regions are formed by repeated treatment with alternating, oppositely charged materials, i.e., by alternating treatment with materials that provide positive and negative surface charges. The layers self-assemble by means of electrostatic layer-by-layer deposition, thus forming a multilayered region over the substrate.

As noted above, the multilayer regions of the present invention typically include the following: (a) a plurality of charged nanoparticle layers, which contain charged nanoparticles, and (b) a plurality of charged polyelectroyte layers, which contain one or more charged polyelectrolyte species.

The nanoparticles for use in the charged nanoparticle layers of the present invention can vary widely in size, but typically have at least one dimension (e.g., the thickness for a nanoplates, the diameter for a nanospheres, nanocylinders and nanotubes, etc.) that is less than 1000 nm, more typically less than 100 nm. Hence, for example, nanoplates typically have at least one dimension that is less than 1000 nm, nanofibers typically have at least two orthogonal dimensions (e.g., the diameter for cylindrical nanofibers) that are less than 1000 nm, while other nanoparticles typically have three orthogonal dimensions that are less than 1000 nm (e.g., the diameter for nanospheres).

A wide variety of nanoparticles are available for use in the charged nanoparticle layers of the present invention including, for example, carbon, ceramic and metallic nanoparticles including nanoplates, nanotubes, and nanospheres, and other nanoparticles. Specific examples of nanoplates include synthetic or natural phyllosilicates including clays and micas (which may optionally be intercalated and/or exfoliated) such as montmorillonite, hectorite, hydrotalcite, vermiculite and laponite. Specific examples of nanotubes and nanofibers include single-wall, so-called "few-wall," and multi-wall carbon nanotubes, such as fullerene nanotubes, vapor grown carbon fibers, alumina nanofibers, titanium oxide nanofibers, tungsten oxide nanofibers, tantalum oxide nanofibers, zirconium oxide nanofibers, and silicate nanofibers such as aluminum silicate nanofibers. Specific examples of further nanoparticles (e.g., nanoparticles having three orthogonal dimensions that are less than 1000 nm) include fullerenes (e.g., "Buckey balls"), silica nanoparticles, aluminum oxide nanoparticles, titanium oxide nanoparticles, tungsten oxide nanoparticles, tantalum oxide nanoparticles, zirconium oxide nanoparticles, dendrimers, and monomeric silicates such as polyhedral oligomeric silsequioxanes (POSS), including various functionalized POSS and polymerized POSS.

One preferred group of nanoparticles for the practice of the present invention are carbon nanotubes and carbon nanofibers having a diameter ranging from 0.5 nm to 200 nm.

In this regard, carbon nanotubes, especially single-wall carbon nanotubes (SWNT), have remarkable mechanical properties, and show great promise for enhancing strength in composites, such as polymer composites. SWNT polymer composites are commonly prepared by polymer blending or by in situ polymerization techniques. Unfortunately, even with surface modification of the SWNT, phase separation is problematic due to the vastly different molecular mobilities of the components. To overcome phase separation issues between the SWNT and the polymer, layer-by-layer assembly has been used in which alternating layers of SWNT and polymeric material have been deposited. See Arif A. Mamedov et al., "Molecular design of strong single-wall carbon nanotube/polyelectrolyte multilayer composites," *Nature Material*, Vol. 1, No. 3, 2002, pages 191-194, the entire disclosure of which is incorporated by reference.

As with the substrate, various techniques are available for providing charges on nanoparticles that are not inherently charged. For example, a surface charge can be provided by adsorbing or otherwise attaching species on the nanoparticles which have a net positive or negative charge, for example, charged amphiphilic substance such as amphiphilic polyelectrolytes and cationic and anionic surfactants (see above). Moreover, where the nanoparticles are sufficiently stable, surface charges can sometimes be established by exposure to highly acidic conditions. For example, it is known that carbon nanoparticles, such as carbon nanotubes, can be partially oxidized by refluxing in strong acid to form carboxylic acid groups (which ionize to become negatively charged carboxyl groups) on the nanoparticles. Establishing a surface charge on nanoparticles is also advantageous in that a relatively stable and uniform suspension of the nanoparticles is commonly achieved, due at least in part to electrostatic stabilization effects.

With respect to polyelectrolyte species, a wide variety of these materials are also available for use in forming charged polyelectrolyte layers in accordance with the present invention. Polyelectrolytes are polymers having charged (e.g., ionically dissociable) groups. Usually, the number of these groups in the polyelectrolytes is so large that the polymers are soluble in polar solvents (including water) when in ionically dissociated form (also called polyions). Depending on the type of dissociable groups, polyelectrolytes are typically classified as polyacids and polybases. When dissociated, polyacids form polyanions, with protons being split off. Polyacids include inorganic, organic and biopolymers. Examples of polyacids are polyphosphoric acids, polyvinylsulfuric acids, polyvinylsulfonic acids, polyvinylphosphonic acids and polyacrylic acids. Examples of the corresponding salts, which are also called polysalts, are polyphosphates, polyvinylsulfates, polyvinylsulfonates, polyvinylphosphonates and polyacrylates. Polybases contain groups which are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations. Some polyelectrolytes have both anionic and cationic groups, but nonetheless have a net positive or negative charge.

Suitable polyelectrolytes for use in accordance with the invention include those based on biopolymers, for example, alginic acid, gummi arabicum, nucleic acids, pectins and proteins, chemically modified biopolymers such as carboxymethyl cellulose and lignin sulfonates, and synthetic polymers such as polymethacrylic acid, polyvinylsulfonic acid, polyvinylphosphonic acid and polyethylenimine. Linear or branched polyelectrolytes can be used in some embodiments. Using branched polyelectrolytes can lead to less compact polyelectrolyte multi layers having a higher degree of wall porosity. Polyelectrolyte molecules can be crosslinked within or/and between the individual layers in some embodiments, e.g. by crosslinking amino groups with aldehydes, for example, to increase stability. Furthermore, amphiphilic polyelectrolytes, e.g., amphiphilic block or random copolymers having partial polyelectrolyte character, can be used in some embodiments to affect permeability towards polar small molecules.

Suitable polyelectrolytes include low-molecular weight polyelectrolytes (e.g., polyelectrolytes having molecular weights of a few hundred Daltons) up to macromolecular polyelectrolytes (e.g., polyelectrolytes of synthetic or biological origin, which commonly have molecular weights of several million Daltons).

Specific examples of polyelectrolyte cations (polycations) include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations. Specific examples of polyelectrolyte anions (polyanions) include poly(styrenesulfonate) polyanions (e.g., poly(sodium styrene sulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions.

In some embodiments, biodisintegrable polyelectrolytes are utilized. For example, by using polyelectrolytes that are biodisintegrable near the outer surface of the multilayer region, a therapeutic agent can be released into the subject at a rate that is dependent upon the rate of disintegration of the polyelectrolyte layers. As used herein, a "biodisintegrable material" is a material which undergoes dissolution, degradation, resorption and/or other disintegration processes over the period that the device is designed to reside in a patient. Conversely, in some embodiments, biostable polyelectrolytes are utilized. As used herein, a "biostable material" is a material which does not undergo substantial dissolution, degradation, resorption and/or other disintegration processes over the period that the device is designed to reside in a patient.

Examples of biodisintegrable and biostable polyelectrolytes include polyglycolic acid (PGA), polylactic acid (PLA), polyamides, poly-2-hydroxy-butyrate (PHB), polycaprolactone (PCL), poly(lactic-co-glycolic)acid (PLGA), protamine sulfate, polyallylamine, polydiallyldimethylammonium species, polyethyleneimine, chitosan, eudragit, gelatin, spermidine, albumin, polyacrylic acid, sodium alginate, polystyrene sulfonate, hyaluronic acid, carrageenan, chondroitin sulfate, carboxymethylcellulose, heparin, other polypeptides and proteins, and DNA, among others.

In some embodiments of the invention, at least one therapeutic agent is disposed on or within the polyelectrolyte multilayer region of the medical devices of the present invention. Several techniques are available for establishing the therapeutic agent within the multilayer region.

In some embodiments, the therapeutic agent is charged, for example, because it is itself a charged molecule or because it is intimately associated with a charged molecule. Examples of charged therapeutic agents include small molecule and polymeric therapeutic agents containing ionically dissociable groups, for example, therapeutic agents containing carboxylic, phosphonic, phosphoric, sulfuric, sulfonic, or other acid groups, or therapeutic agents containing amine, imine or another basic groups. As noted above, acidic groups generally become anionic groups in aqueous solution by donating protons, while basic groups generally become cations by accepting protons. In some cases, the therapeutic agent will contain both acidic and basic groups, yet will have a net (overall) charge. Examples of charged therapeutic agents include polynucleotides (e.g., DNA and RNA), polypeptides (e.g., proteins, whose overall net charge will vary with pH, based on their respective isoelectric points), and various small molecule drugs, among others. For example, insulin is a negatively charged molecule at neutral pH, while protamine is positively charged. Other examples include heparin, hyaluronan, immunogloubulins and so forth.

Even where the therapeutic agent does not possess one or more charged groups, it can nevertheless be provided with a charge, for example, through non-covalent association with a charged species. Examples of non-covalent associations include hydrogen bonding, hydrophilic/lipophilic interactions, and so forth. For instance, the therapeutic agent can be associated with an ionic amphiphilic substance, such as one of those set forth above.

In certain embodiments where a charged therapeutic agent is employed, one or more layers of the charged therapeutic agent is/are deposited during the course of assembling the multilayer region. For example, in some instances, the therapeutic agent is itself a polyelectrolyte (e.g., where the therapeutic agent is a polypeptide or a polynucleotide) and it is used, as such, to create one or more polyelectrolyte layers within the multilayer region. In other instances, the charged therapeutic agent is not a polyelectrolyte (e.g., it may be a charged small molecule drug). Nevertheless, one or more layers of the charged therapeutic agent can be substituted for one or more layers of the same charge (i.e., positive or negative) during the multilayer assembly process. In each of the above cases, the therapeutic agent is disposed on and/or within the multilayer region.

In still other embodiments, the therapeutic agent is provided within charged nanocapsules, which are formed, for example, using layer-by-layer techniques such as those described herein and in commonly assigned U.S. Ser. No. 10/768,388, entitled "Localized Drug Delivery Using Drug-Loaded Nanocapsules," the entire disclosure of which is incorporated by reference. In these embodiments, one or more layers of the charged nanocapsules can be deposited during the course of assembling the multilayer region.

In still other embodiments, the multilayer region is loaded with therapeutic agent subsequent to its formation. In this regard, various techniques have been reported for incorporating therapeutic agents into pre-formed microscopic polyelectrolyte multilayer capsules, and these techniques are equally applicable to the multilayer-coated structures of the present invention.

For example, techniques are known in the polyelectrolyte multilayer art for increasing the porosity, and thus the permeability, of polyelectrolyte multilayer structures. For instance, techniques have been reported for introducing different materials into polyelectrolyte multilayer capsules by varying the pH. In particular, polyelectrolyte multilayer structures are known (e.g. PSS-PAH multilayer structures) which are effectively closed at higher pH's. However, at more acidic pH's (e.g., pH 6 and below). the multilayer structures open up, allowing macromolecules (e.g., FITC-labeled dextran, MW~75,000 and MW~2,000,000 as well as FITC-labeled albumin have been demonstrated) to freely permeate the capsule. See, e.g., Antipov, A. A. et al., "Polyelectrolyte multilayer capsule permeability control," *Colloids and Surfaces A: Physicochemical and Engineering Aspects,* 198-200 (2002) pp. 535-541.

In the present invention, layer-by-layer assembly is preferably conducted by exposing a selected charged substrate to solutions or suspensions that contain species of alternating net charge, including solutions or suspensions that contain charged nanoparticles, charged polyelectrolytes, and, optionally, charged therapeutic agents. The concentration of the charged entities within these solutions and suspensions can vary widely, but will commonly be in the range of from 0.01 to 10 mg/ml, and more commonly from 0.1 to 1 mg/ml. Moreover the pH of these suspensions and solutions are such that the nanoparticles, polyelectrolytes, and optional therapeutic agents maintain their desired charge. Buffer systems may be employed for this purpose, if needed, although the charged entities chosen are commonly ionized at neutral pH (e.g., at pH 6-8) or at the pH of the body location where the device is to be inserted or implanted.

The solutions and suspensions containing the charged species (e.g., solutions/suspensions of polyelectrolytes, charged nanoparticles, or other optional charged species such as charged therapeutic agents) can be applied to the charged substrate surface using a variety of techniques including, for example, spraying techniques, dipping techniques, roll and brush coating techniques, techniques involving coating via mechanical suspension such as air suspension, ink jet techniques, spin coating techniques, web coating techniques and combinations of these processes. As a specific example, layers can be applied over an underlying substrate by immersing the entire substrate into a solution or suspension containing the charged species, or by immersing half of the substrate into the solution or suspension, flipping the same, and immersing the other half of the substrate into the solution or suspension to complete the coating. In some embodiments, the substrate is rinsed after application of each charged species layer, for example, using a washing solution that has a pH that will ensure that the charge of the outer layer is maintained.

Using these and other techniques, multiple layers of alternating charge are applied over the underlying substrate, including the application of one or more (typically a plurality of) charged nanoparticle layers and the application of one or more (typically a plurality of) charged polyelectroyte layers. For example, in some embodiments, between 10 and 200, more typically between 30 and 100 layers are applied over the substrate. The total thickness of the multilayer region that is assembled will typically range, for example, from 10 nanometers to 40 micrometers (microns), more typically between 100 nanometers and 10 microns.

In many beneficial embodiments, the multilayer region comprises an alternating series of negatively charged nanoparticle layers and positively charged polyelectroyte layers. In other beneficial embodiments, the multilayer region comprises an alternating series of positively charged nanoparticle layers and negatively charged polyelectroyte layers. In still other beneficial embodiments, the multilayer region comprises an alternating series of positively and negatively charged nanoparticle layers. One class of nanoparticles that come both in positively and negatively charged forms are dendrimers.

One preferred material for use in forming charged polyelectroyte layers in accordance with the present invention is polyethyleneimine (PEI), which, as noted above, is an amphiphilic polyelectrolyte and thus is useful for establishing an initial charged layer on a substrate and can be used to provide subsequent polyelectrolyte layers as well. Being positively charged, PEI is useful in combination with adjacent layers that contain negatively charged species, for example, carboxyl functionalized carbon nanotubes. PEI having a molecular weight of about 70,000 is readily available from Sigma Aldrich. For example, to form a multilayer stack, the substrate can be dipped in a solution of PEI, followed by dipping in a suspension of carbon nanotubes, and so forth, with the number of alternating layers established ultimately depending, for example, upon the desired thickness and strength of the final multilayer region.

The PEI layer can also be followed by a layer of a negatively charged polyelectrolyte such as polyacrylic acid (PAA). The negatively charged polyelectrolyte is useful, for instance, in combination with adjacent layers that contain positively charged species, such as positively charged nanoparticles, for example dendrimers and functionalized gold nanoparticles, or additional PEI layers (e.g., where it is desired to establish multiple polyelectrolyte layers beneath, between or above the nanoparticle layers).

With respect to functionalized gold nanoparticles, it is noted that these particles could help to create a radio-opaque layer. Gold nanoparticles can be made positively charged by applying a outer layer of lysine to the same. See, for example, "DNA-mediated electrostatic assembly of gold nanoparticles into linear arrays by a simple drop-coating procedure," Murali Sastrya and Ashavani Kumar, *Applied Physics Letters*, Vol. 78, No. 19, 7 May 2001.

The bonding between a substrate and PEI can be enhanced, for example, by providing as substrate with negatively charged groups. For example, a Pebax® balloon surface can be modified to have a negative charge by providing the balloon with negatively charged functional groups such as carboxylate groups.

As noted above, in some embodiments, a multilayer region is formed upon an underlying substrate that becomes incorporated into the finished medical device. As one specific example, a multilayer region with reinforcement properties in accordance with the present invention can be built upon a preexisting balloon, such as a Pebax® balloon.

In some embodiments, on the other hand, the underlying substrate merely acts as a template (e.g., as a mold) for application of the layer-by-layer technique, and the multilayer region is freed from the substrate after forming the multilayer region. The multilayer region is applied in some instance to the inside of the removable substrate, and is applied in other instances to the outside of the removable substrate.

In some cases, the removable substrate is releasably engaged with the multilayer region, for example, by forming a weak (dissolvable) first electrostatic layer on top the substrate. As another example, hollow capsules have been formed by forming a series of polyelectrolyte multi layers around cores of melamine formaldehyde or manganese carbonate, followed by removal of the core material by dissolution. See Sukhorukov et al., "Comparative Analysis of Hollow and Filled Polyelectrolyte Microcapsules Templated on Melamine Formaldehyde and Carbonate Cores," *Macromol. Chem. Phys.*, 205, 2004, pp. 530-535. Using analogous procedures, a layer of melamine formaldehyde or manganese carbonate is formed on a removable substrate. After forming the desired polyelectrolyte layers on the substrate, the layer of melamine formaldehyde or manganese carbonate is dissolved, releasing the substrate. The substrate can be in the form, for instance, of a reusable one-piece or multi-piece (e.g. two-piece) mold, as is known in the art.

In other cases, the substrate is removed by destroying it, for example, by melting, sublimation, combustion, dissolution or other process, in order to free the multilayer region. For instance, in some embodiments, a so-called "lost core" mold is used. These molds can be made, for example, from materials that melt at moderately elevated temperatures (e.g., 60° C.), for instance, dental waxes such as those available from MDL Dental Products, Inc., Seattle, Wash., USA. Other examples of materials that can be used for the formation of destroyable molds are materials that are essentially insoluble in cold water, but are soluble in hot water. Polyvinyl alcohol (PVOH) is one example of such a material.

Where the multilayer region is provided over a substrate, it can extend over all or only a portion of the substrate. For example, multilayer regions can be provided over multiple surface portions of an underlying substrate and may be provided in any shape or pattern (e.g., in the form of a series of rectangles, stripes, or any other continuous or noncontinuous pattern). Techniques by which patterned multilayer regions may be provided are described above and include ink jet techniques, roll coating techniques, etc. For example, in some embodiments, a patterned multilayer region is created, to provide differences in strength or functionality across the medical device.

In some embodiments, one or more reinforcement members are provided adjacent to or within the multilayer regions of the present invention. For example, in some cases, one or more reinforcement members are applied to an underlying substrate, followed by a series of polyelectrolyte and nanoparticle layers. As another example, in some cases, a first series of polyelectrolyte layers or a first series of both polyelectrolyte and nanoparticle layers are provided, followed by the application of one or more reinforcement members, followed by a second series of polyelectrolyte layers or a second series of both polyelectrolyte and nanoparticle layers.

Examples of reinforcement members include fibrous reinforcement members such as metal fiber meshes, metal fiber braids, metal fiber windings, intermingled fibers (e.g., metal fiber, carbon fibers, high density polyethylene fibers, liquid polymer crystals) and so forth. Metals that can be used for this purpose include, for example, various metals listed above for use in forming metallic substrates. For example, very fine steel wire is available from Bekaert (Belgium) for use as a reinforcement member. If desired, the reinforcement members can be provided with a surface charge to enhance incorporation of the reinforcement members onto or into the multilayer regions. For example, layer-by-layer techniques such as those described herein can be used to encapsulate the reinforcement members, thereby providing them with a charged outer layer and enhancing interaction of the reinforcement members with an adjacent layer (e.g., a polyelectrolyte or nanoparticle layer) of opposite charge.

A variety of outer top layers can be provided for the multilayer regions of the present invention. For instance, in some embodiments, the outer top layer is a charged nanoparticle layer, a charged polyelectrolyte layer, charged therapeutic agent layer, and so forth. As a specific example, the outer top layer can be a carbon nanoparticle layer (e.g., a layer of charged carbon nanotubes, C60 "Buckey balls", etc.).

In other embodiments, an outer polymer layer is provided over the multilayer region (e.g., using conventional thermoplastic or solvent processing techniques) to protect the outer surface of the multilayer region and to contain any debris in the unlikely event that the multilayer region becomes damaged (e.g., in the unlikely event of a balloon burst). Such polymer layers can be selected from the various polymeric materials described above for use in connection with substrates.

As indicated above, in some embodiments of the invention, one or more therapeutic agents are incorporated onto or into the multilayer region, giving the medical device, for example, a drug releasing function upon implantation.

Therapeutic agents may be used singly or in combination in the medical devices of the present invention. "Drugs," "therapeutic agents," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, antibodies recognizing receptors on endothelial progenitor cells, proteins of the tetraspanin family, such as CD9 Beta-1 and Beta-3 integrins, CD63, CD81, FcgammaRII, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; and (r) hormones.

Preferred non-genetic therapeutic agents include paclitaxel, sirolimus, everolimus, tacrolimus, dexamethasone, estradiol, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP'S"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the medical device including the nature of its multilayer region(s), and so forth.

Further specific embodiments of the invention will now be described with reference to the Figures.

Figure 1A:
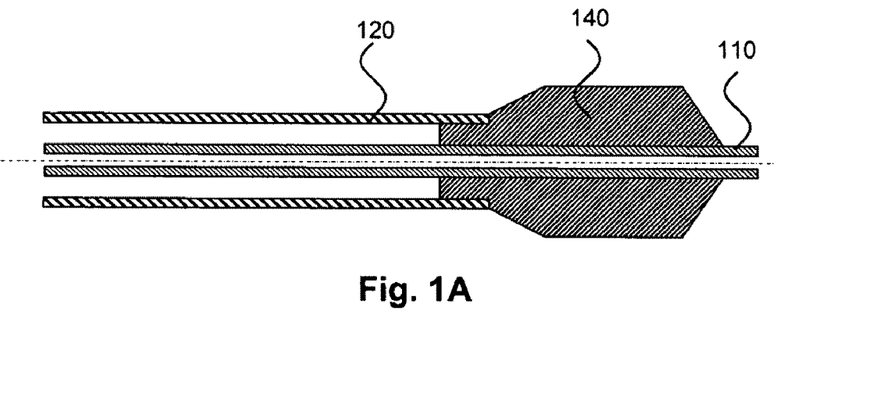
FIGS. 1A-1C are schematic illustrations that show a process for forming a balloon catheter, in accordance with an embodiment of the present invention.
Figure 1B:
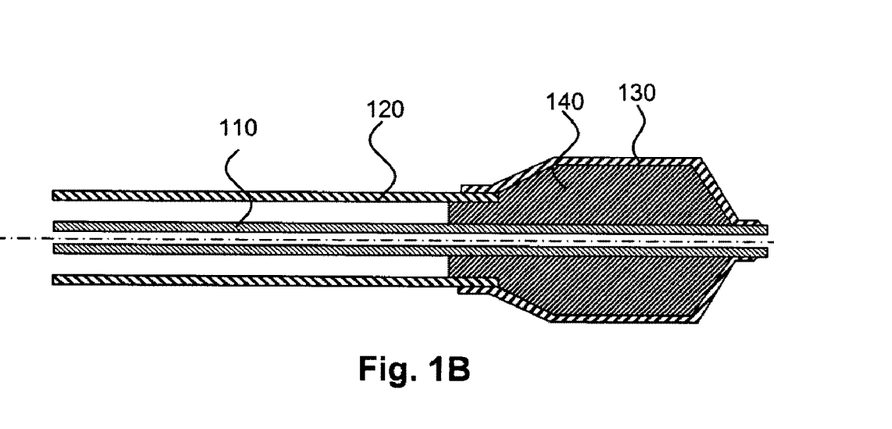
Figure 1C:
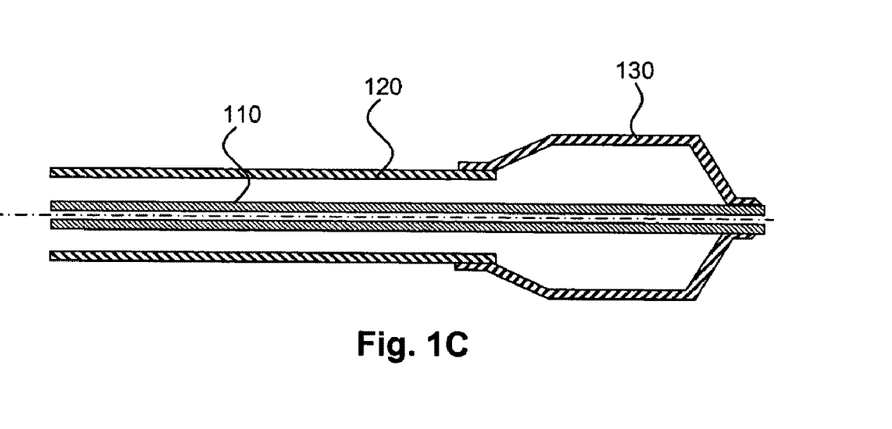

Referring now to FIGS. 1A-1C, one embodiment of the construction of a balloon catheter will now be described. Because polyelectrolyte multilayers containing SWNT have been measured to have an ultimate strength of 220 Mpa (similar to PET film), the embodiment of the invention described in these figures utilizes a destroyable mold for the formation of the multilayer region. In other embodiments, of course, the balloon can be made using a substrate that is not ultimately destroyed, such as a two-piece, releasable mold or such as a pre-existing balloon that is incorporated into the device.

Turning now to FIG. 1A, an assembly is illustrated which includes a "lost core" mold 140, an inner guidewire lumen 110 and an outer inflation lumen 120, although it will immediately become clear on one of ordinary skill in the art that the balloon can built independently of the guidewire and inflation lumens. Guidewire and inflation lumens are well known in the art and are commonly formed from materials such as nylons including nylon 12, thermoplastic polyester elastomers (e.g., Hytrel®), polyether-block co-polyamide polymers (e.g., Pebax®), high density polyethylene, and polyurethane. Guidewire lumens are commonly provided with lubricious materials on their inner surfaces, for example, polytetrafluoroethylene or high density polyethylene.

In the next step, a multilayer coating 130, containing multiple alternating layers of polyelectrolyte (e.g., PEI) and nanoparticles (e.g., SWNT), is applied over the mold 140 as illustrated in FIG. 1B. Note that, in this embodiment, the multilayer coating 130 extends beyond the proximal end (left end) of the mold 140, where it engages the outer inflation lumen 120, and extends beyond the distal (right) end of the mold 140, where it engages the inner guidewire lumen 110.

Finally, the mold 140 is removed, thereby providing a finished balloon catheter having an inner guidewire lumen 110, an outer inflation lumen 120, and a multilayer balloon 130 as illustrated in FIG. 1C.

Of course innumerable variations on the above themes are possible.

For example, in the above steps, the multilayer coating 130 is formed not only on the wax mold 140, but also over a portion of the guidewire lumen 110 and the outer inflation lumen 120. As a result a separate step is avoided for sealing the balloon 130 to the lumens 110, 120. In other embodiments, on the other hand, the balloon is independently formed and subsequently attached to the lumens 110, 120.

As another example, a braiding, winding or fiber meshwork, preferably having a charged surface to ensure optimal adherence to subsequently assembled layers, can be provided on top of the wax mold. The braiding, winding or fiber meshwork can also be provided after several polyelectrolyte and/or nanoparticle layers have been deposited, if desired.

As another example, the mold of FIG. 1A can be extended to the proximal side of the assembly (not shown), thereby allowing part of the outer lumen to be constructed using the layer-by-layer technology. In fact, an entire outer lumen can be constructed in this fashion. Similarly, it is also possible to build the tip of the inner lumen in the same fashion.

Figure 3A:
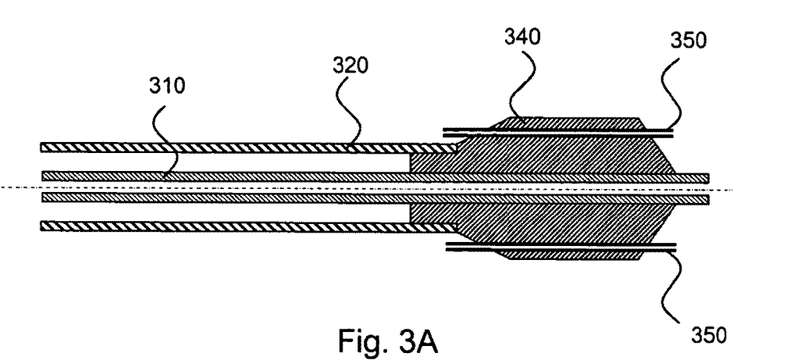
FIGS. 3A-3C are schematic illustrations that show a process for forming a perfusion balloon catheter, in accordance with another embodiment of the present invention.
Figure 3B:
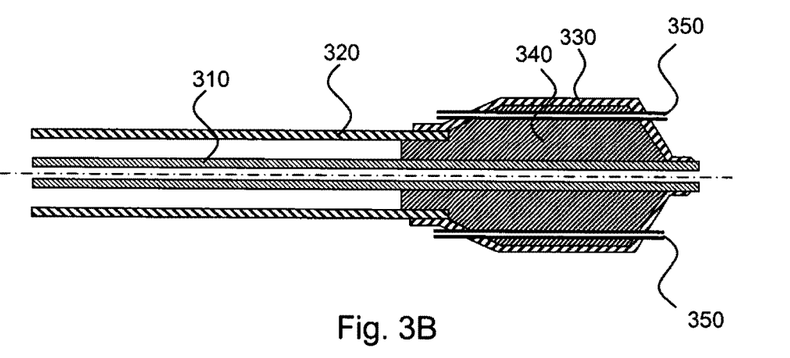
Figure 3C:
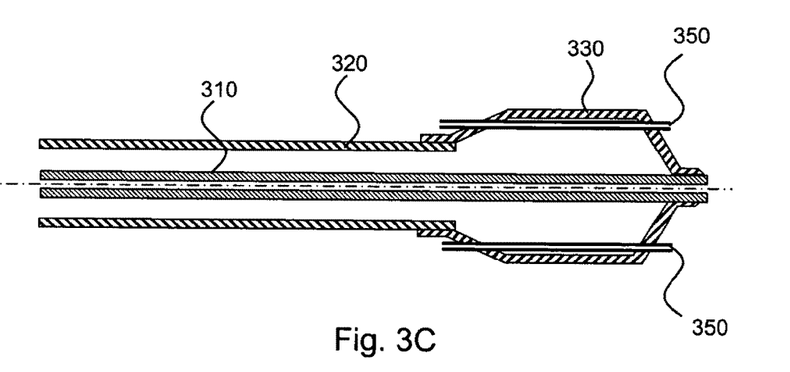

With reference now to FIGS. 3A-3C, in other embodiments, the finished balloon 330 can be provided with longitudinal perfusion channels, for example, by longitudinally placing tubes 350 inside the wax mold 340, as illustrated in the assembly of FIG. 3A. As can be seen from FIG. 3A, the tubes 350 protrude out of both sides of the wax mold 340.

A multilayer coating 330 containing multiple alternating polyelectrolyte and nanoparticle layers is then applied over the assembly as shown in FIG. 3B.

Finally, the wax mold 340 is removed, thereby providing a finished balloon catheter having an inner guidewire lumen 310, an outer inflation lumen 320, and a multilayer balloon 330, as illustrated in FIG. 3C. Note that the tubes 350 are incorporated into the balloon structure, forming perfusion channels. The protruding ends of the tubes 350 are subsequently be trimmed as desired. Note than such tubes 350 can also be used as guidewire lumens, if desired, rendering the inner tube 310 in the structure superfluous.

Balloons made by procedures such as those discussed herein are designed to be flexible, strong, non-compliant and durable (e.g., having good puncture and abrasion resistance). Of course, the present invention has applicability to a wide range of medical devices other than balloon catheters.

Figure 2A:
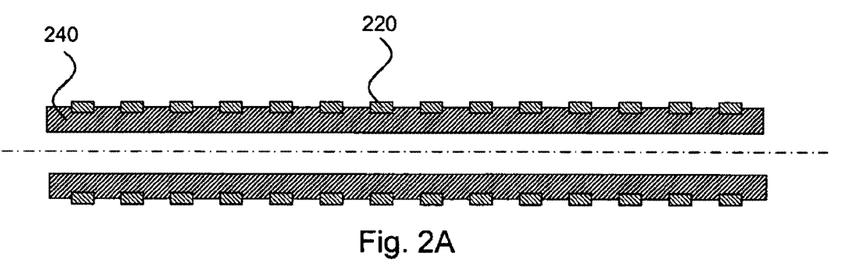
FIGS. 2A-2D are schematic illustrations that show a process for forming a stent draft coating, in accordance with another embodiment of the present invention.

Referring now to FIGS. 2A-2D, the encapsulation of a stent (i.e., the formation of a stent graft) will now be described. As in FIGS. 1A-1C and 3A-3C above, the mold illustrated in FIG. 2A is a removable mold 240 made, for example, from a material such as dental wax. The mold 240 in this embodiment is in the form of an annulus and is positioned inside the stent 220. The outer surfaces of the struts of the stent 220 remain uncovered by the mold 240 as shown.

Figure 2B:
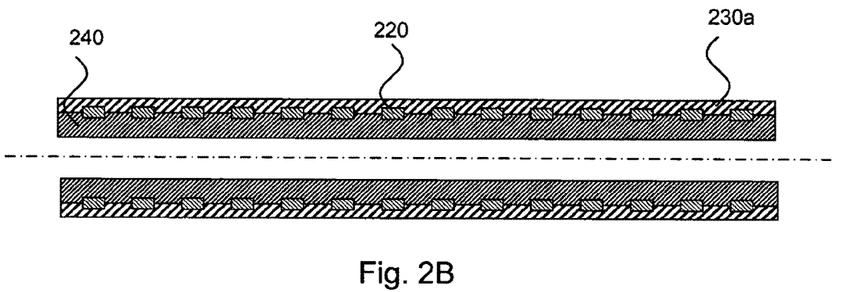

As illustrated in FIG. 2B, a first multilayer coating 230a, which contains multiple alternating polyelectrolyte and nanoparticle layers, is then applied over the mold 240 and stent 220, using, for example, techniques such as those described above.

Figure 2C:
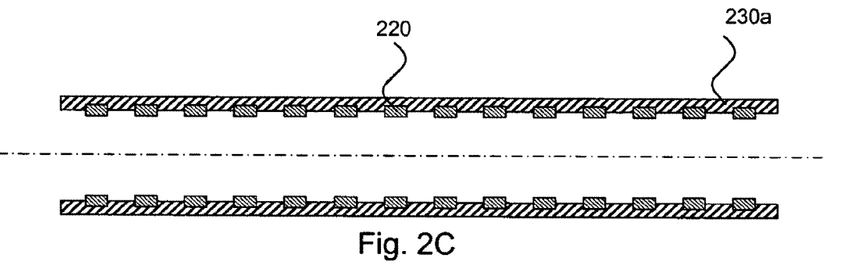

The wax mold 240 is then removed, yielding the structure illustrated in FIG. 2C. Of course, a multilayer coating could be provided on the inside of the stent by placing a mold, or some other removable substrate such as a polymeric wrap, on the outside of the stent structure.

Figure 2D:
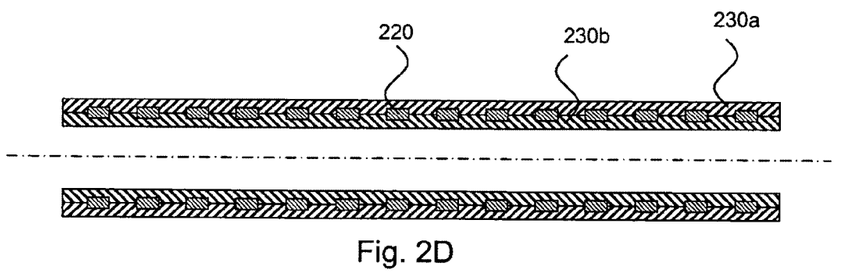

In some embodiments, it is desirable to apply multilayer coatings on both the outside and the inside of the stent structure. For example, a second multilayer coating 230b, which, like coating 230a, contains multiple alternating polyelectrolyte and nanoparticle layers, can be applied to the inside of the structure of FIG. 2C, using the stent 220 and multilayer coating 230a as a substrate for the layer assembly. This yields the encapsulated stent structure of FIG. 2D. Note that the multilayer coating 230a,b extends beyond both ends of the stent 220 in the embodiment shown.

As with the balloons above, innumerable variations on the above themes are possible. For example, instead of using a lost-wax method to build the graft, it is also possible to add additional layers to an existing graft using the techniques described herein.

Stent grafts formed in accordance with the present invention can be delivered to a subject by a variety of known stent delivery systems, including various balloon catheters for stent delivery. In some embodiments, stent grafts can be delivered using a catheter that contains a multilayer balloon, also formed in accordance with the present invention.

EXAMPLE 1

A mold 3 mm in diameter of polyvinyl alcohol (PVOH) series C-5 (purchased from Adept Polymers Limited, London) is insert molded at 190° C. A metal core pin is embedded through the center of the mold.

The following solutions/suspensions are prepared: (I) Polyurethane Pellethane 70D (Dow Chemical, Midland, Mich.) in Tetrahydrofuran (THF) at a concentration of 5%; (2) polyethylenimine (PEI) (Aldrich) in water at a concentration of 1%; (3) polyacrylic acid (PAA) (Aldrich) in water at a concentration of 1%; and (4) carbon nanotubes (CNT) (Carbolex, Inc., Lexington, Ky., USA) in water at a concentration of 0.6%. The CNT are functionalized by refluxing them in nitric acid.

A first layer of the polyurethane is deposited (by dipping) on the PVOH core. Then, a layer of PEI is deposited on top of the polyurethane layer. After this, 204 layers are deposited by repeating the following sequence seventeen times: PAA-PEI-CNT-PEI-CNT-PEI-CNT-PEI-CNT-PEI-CNT-PEI. The PAA layers are introduced to reinforce the electrostatic attraction.

After deposition of the layers, the metal core pin is pulled out of the mold and water at a temperature of 60° C. is flushed for 2 hours through the opening left by the core pin, thus dissolving the PVOH core.

EXAMPLE 2

The procedures of Example 1 are followed, with the following changes: Instead of the core and the first polyurethane layer, an existing PEBAX 7233 single wall balloon (Boston Scientific Corp.) is used as a non-removable substrate. First, a layer of PEI deposited on the balloon. After this, 96 layers are deposited by following the following sequence eight times: PAA-PEI-CNT-PEI-CNT-PEI-CNT-PEI-CNT-PEI-CNT-PEI. As above, the P AA layers reinforce the electrostatic attraction between the layers.

Although various embodiments of the invention are specifically illustrated and described herein, it will be appreciated that modifications and variations of the present invention are covered by the above teachings without departing from the spirit and intended scope of the invention.

The invention claimed is:

1. An expandable medical balloon, the expandable medical balloon comprising:
   (a) a polymer layer, the polymer layer defines a balloon wall comprising an inner surface and an outer surface, the inner surface defining a lumen;
   (b) a multilayer region comprising:
      (i) a charged nanoparticle layer; and
      (ii) a plurality of charged polyelectroyte layers comprising charged polyelectrolyte species; and
   (c) a therapeutic agent disposed on or within the multilayer region.

2. The expandable medical balloon of claim 1 wherein said charged nanoparticle layer comprises at least one member selected from the group consisting of carbon nanotubes, carbon nanofibers, fullerenes, ceramic nanotubes, ceramic nanofibers, phyllosilicates, monomeric silicates and dendrimers.

3. The expandable medical balloon of claim 1 wherein a surface charge is provided on the polymer layer by exposing the polymer layer to a charged amphiphilic substance.

4. The expandable medical balloon of claim 3 wherein the amphiphilic substance comprises at least one of poly(styrene sulfonate) or polyethylene imine.

5. The expandable medical balloon of claim 4 wherein the amphiphilic substance is polyethylene imine.

6. The expandable medical balloon of claim 1 wherein a surface charge is provided on the polymer layer by exposing the polymer layer to a cationic or anionic substance.

7. The expandable medical balloon of claim 1 wherein the plurality of charged polyelectrolyte layers comprises polyethylene imine or polyacrylic acid.

8. The expandable medical balloon of claim 1 wherein said polymer layer comprises poly(ether-block-amide) or polyurethane.

9. The expandable medical balloon of claim 8 wherein said polymer layer comprises poly(ether-block-amide).

10. The expandable medical balloon of claim 8 wherein said polymer layer comprises polyurethane.

11. The expandable medical balloon of claim 8 wherein said multilayer region comprises alternating layers of carbon nanotubes, polyacrylic acid and polyethylene imine.

12. The expandable medical balloon of claim 11 wherein the multilayer region comprises a first layer of polyethylene imine, the polyethylene imine is deposited on the poly(ether-block-amide).

13. The expandable medical balloon of claim 12 wherein the multilayer region comprises a second layer of polyacrylic acid, the polyacrylic acid is deposited on the first layer of polyethylene imine.

14. The expandable medical balloon of claim 1 wherein said polymer layer is provided with functional groups having a negative charge.

15. The expandable medical balloon of claim 14 wherein said functional groups comprise a member selected from the group consisting of a carboxylic, phosphonic, phosphoric, sulfuric and sulfonic.

16. The expandable medical balloon of claim 1 wherein said therapeutic agent is selected from antithrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

17. The expandable medical balloon of claim 16 wherein the therapeutic agent is provided with a charge.

18. The expandable medical balloon of claim 17 wherein the therapeutic agent comprises functional groups at least one of which is a member selected from the group consisting of carboxylic, phosphonic, phosphoric, sulfuric and sulfonic.

19. The expandable medical balloon of claim 17 wherein the therapeutic agent comprises functional groups at least one of which is a member selected from the group consisting of amine and imine.

20. The expandable medical balloon of claim 1 wherein the therapeutic agent is charged and comprises at least one member selected from the group consisting of polynucleotides and polypeptides.

\* \* \* \* \*